United States Patent
Agassi et al.

(10) Patent No.: US 11,675,805 B2
(45) Date of Patent: Jun. 13, 2023

(54) CONCEPT AGNOSTIC RECONCILATION AND PRIORITIZATION BASED ON DETERMINISTIC AND CONSERVATIVE WEIGHT METHODS

(71) Applicant: CERNER INNOVATION, INC., Kansas City, KS (US)

(72) Inventors: Natalee Agassi, Blue Bell, PA (US); Joseph Francis Bartelmo, Spring City, PA (US); Todd Wyeth Fritsche, Phoenixville, PA (US); William John Ormerod, Jr., Fairfax, VT (US)

(73) Assignee: Cerner Innovation, Inc., Kansas City, MO (US)

( * ) Notice: Subject to any disclaimer, the term of this patent is extended or adjusted under 35 U.S.C. 154(b) by 10 days.

(21) Appl. No.: 16/715,640

(22) Filed: Dec. 16, 2019

(65) Prior Publication Data
US 2021/0182306 A1    Jun. 17, 2021

(51) Int. Cl.
*G06F 16/25* (2019.01)
*G06F 16/906* (2019.01)
*G16H 15/00* (2018.01)
*G06F 16/174* (2019.01)
*G06F 16/11* (2019.01)

(52) U.S. Cl.
CPC .......... *G06F 16/258* (2019.01); *G06F 16/125* (2019.01); *G06F 16/1748* (2019.01); *G06F 16/906* (2019.01); *G16H 15/00* (2018.01)

(58) Field of Classification Search
CPC .. G06F 16/125; G06F 16/1748; G06F 16/215; G06F 16/258; G06F 16/285; G06F 16/906; G16H 15/00
See application file for complete search history.

(56) References Cited

U.S. PATENT DOCUMENTS

| | | |
|---|---|---|
| 4,847,764 A | 7/1989 | Halvorson et al. |
| 5,072,383 A | 12/1991 | Brimm et al. |
| 5,077,666 A | 12/1991 | Brimm et al. |
| 5,530,861 A | 6/1996 | Diamant et al. |
| 5,692,125 A | 11/1997 | Schloss et al. |
| 5,721,913 A | 2/1998 | Ackroff et al. |
| 5,745,901 A | 4/1998 | Entner et al. |

(Continued)

FOREIGN PATENT DOCUMENTS

| | | |
|---|---|---|
| EP | 0090971 A1 | 10/1983 |
| EP | 3950971 A2 | 10/1999 |

(Continued)

OTHER PUBLICATIONS

Final Office Action received for U.S. Appl. No. 16/233,348, dated Dec. 24, 2021, 52 pages.

(Continued)

*Primary Examiner* — Anhtai V Tran
*Assistant Examiner* — Xiaoqin Hu
(74) *Attorney, Agent, or Firm* — Invoke

(57) ABSTRACT

Methods, systems, and computer-readable media are disclosed herein to provide rule-based reconciliation of records. Specifically, rules are utilized to reconcile one or more records and identify duplicates therein. Once duplicate records are identified, one or more ranking sets can be utilized to identify which of the duplicate records to write to the system.

20 Claims, 8 Drawing Sheets

(56) References Cited

U.S. PATENT DOCUMENTS

| | | | |
|---|---|---|---|
| 5,758,095 A | 5/1998 | Albaum et al. |
| 5,784,635 A | 7/1998 | Mccallum |
| 5,790,119 A | 8/1998 | Sklut et al. |
| 5,799,297 A | 8/1998 | Goodridge et al. |
| 5,826,239 A | 10/1998 | Du et al. |
| 5,832,455 A | 11/1998 | Hayashi et al. |
| 5,842,173 A | 11/1998 | Strum et al. |
| 5,842,976 A | 12/1998 | Williamson |
| 5,911,687 A | 6/1999 | Sato et al. |
| 5,923,018 A | 7/1999 | Kameda et al. |
| 5,937,388 A | 8/1999 | Davis et al. |
| 5,970,463 A | 10/1999 | Cave et al. |
| 5,987,422 A | 11/1999 | Buzsaki |
| 5,991,728 A | 11/1999 | Debusk et al. |
| 6,014,629 A | 1/2000 | Debruin-ashton |
| 6,037,940 A | 3/2000 | Schroeder et al. |
| 6,052,669 A | 4/2000 | Smith et al. |
| 6,052,684 A | 4/2000 | Du |
| 6,061,506 A | 5/2000 | Wollaston et al. |
| 6,064,984 A | 5/2000 | Ferguson et al. |
| 6,067,548 A | 5/2000 | Cheng |
| 6,072,493 A | 6/2000 | Driskell et al. |
| 6,078,982 A | 6/2000 | Du et al. |
| 6,085,184 A | 7/2000 | Bertrand et al. |
| 6,088,679 A | 7/2000 | Barkley |
| 6,115,646 A | 9/2000 | Fiszman et al. |
| 6,151,583 A | 11/2000 | Ohmura et al. |
| 6,208,345 B1 | 3/2001 | Sheard et al. |
| 6,208,974 B1 | 3/2001 | Campbell et al. |
| 6,223,164 B1 | 4/2001 | Seare et al. |
| 6,225,998 B1 | 5/2001 | Okita et al. |
| 6,278,901 B1 | 8/2001 | Winner et al. |
| 6,279,009 B1 | 8/2001 | Smirnov et al. |
| 6,304,886 B1 | 10/2001 | Bernardo et al. |
| 6,308,163 B1 | 10/2001 | Du et al. |
| 6,308,188 B1 | 10/2001 | Bernardo et al. |
| 6,311,192 B1 | 10/2001 | Rosenthal et al. |
| 6,314,556 B1 | 11/2001 | Debusk et al. |
| 6,347,329 B1 | 2/2002 | Evans |
| 6,349,329 B1 | 2/2002 | Mackintosh et al. |
| 6,430,538 B1 | 8/2002 | Bacon et al. |
| 6,458,080 B1 | 10/2002 | Brown et al. |
| 6,484,144 B2 | 11/2002 | Martin et al. |
| 6,697,784 B2 | 2/2004 | Bacon et al. |
| 6,728,947 B1 | 4/2004 | Bengston |
| 6,912,549 B2 | 6/2005 | Rotter et al. |
| 6,915,265 B1 | 7/2005 | Johnson |
| 6,966,049 B2 | 11/2005 | Lepejian et al. |
| 6,970,844 B1 | 11/2005 | Bierenbaum |
| 6,978,268 B2 | 12/2005 | Thomas et al. |
| 7,027,997 B1 | 4/2006 | Robinson et al. |
| 7,035,862 B2 | 4/2006 | Patitucci |
| 7,047,535 B2 | 5/2006 | Lee et al. |
| 7,051,012 B2 | 5/2006 | Cole et al. |
| 7,136,824 B2 | 11/2006 | Masuda et al. |
| 7,181,375 B2 | 2/2007 | Rao et al. |
| 7,184,967 B1 | 2/2007 | Mital et al. |
| 7,240,324 B2 | 7/2007 | Casati et al. |
| 7,275,039 B2 | 9/2007 | Setteducati |
| 7,296,056 B2 | 11/2007 | Yaung |
| 7,318,059 B2 | 1/2008 | Thomas et al. |
| 7,403,936 B2 | 7/2008 | Giang et al. |
| 7,428,495 B2 | 9/2008 | Dhar et al. |
| 7,437,302 B2 | 10/2008 | Haskell et al. |
| 7,447,644 B2 | 11/2008 | Brandt et al. |
| 7,457,731 B2 | 11/2008 | Rao |
| 7,457,765 B2 | 11/2008 | Thompson et al. |
| 7,590,932 B2 | 9/2009 | Britton et al. |
| 7,617,078 B2 | 11/2009 | Rao et al. |
| 7,630,947 B2 | 12/2009 | Pandya et al. |
| 7,653,566 B2 | 1/2010 | Kim et al. |
| 7,689,441 B1 | 3/2010 | Craft |
| 7,711,404 B2 | 5/2010 | Rao et al. |
| 7,725,330 B2 | 5/2010 | Rao et al. |
| 7,744,540 B2 | 6/2010 | Rao et al. |
| 7,756,728 B2 | 7/2010 | Maughan et al. |
| 7,805,385 B2 | 9/2010 | Steck et al. |
| 7,840,511 B2 | 11/2010 | Rosales et al. |
| 7,844,560 B2 | 11/2010 | Krishnan et al. |
| 7,877,272 B2 | 1/2011 | Rosales et al. |
| 7,890,349 B2 | 2/2011 | Cole et al. |
| 7,895,055 B2 | 2/2011 | Schneider et al. |
| 7,917,377 B2 | 3/2011 | Rao et al. |
| 7,937,655 B2 | 5/2011 | Teng et al. |
| 3,000,978 A1 | 8/2011 | Wager et al. |
| 8,027,849 B2 | 9/2011 | Johnson et al. |
| 8,046,362 B2 * | 10/2011 | Bayliss ................ G06F 16/215 |
| | | 707/737 |
| 8,200,527 B1 | 6/2012 | Thompson et al. |
| 8,214,224 B2 | 7/2012 | Rao et al. |
| 8,214,225 B2 | 7/2012 | Rao et al. |
| 8,219,416 B2 | 7/2012 | Auker et al. |
| 8,280,750 B2 | 10/2012 | Krishnan et al. |
| 8,326,667 B2 | 12/2012 | Johnson |
| 8,392,152 B2 | 3/2013 | Rao |
| 8,392,232 B2 | 3/2013 | Mcgillin |
| 8,571,884 B2 | 10/2013 | Badgett et al. |
| 8,579,784 B2 | 11/2013 | Krishnan et al. |
| 8,768,741 B1 | 7/2014 | Hinton et al. |
| 8,775,207 B2 | 7/2014 | Abraham et al. |
| 9,336,283 B2 | 5/2016 | Giang et al. |
| 9,639,662 B2 | 5/2017 | Sethumadhavan et al. |
| 9,703,927 B2 | 7/2017 | Chaudhri et al. |
| 9,824,316 B2 | 11/2017 | Junker et al. |
| 2001/0001144 A1 | 5/2001 | Kapp |
| 2001/0032108 A1 | 10/2001 | Sieron et al. |
| 2001/0037227 A1 | 11/2001 | Mcinnis et al. |
| 2002/0018066 A1 | 2/2002 | Vizer |
| 2002/0059201 A1 | 5/2002 | Work |
| 2002/0059251 A1 | 5/2002 | Stern et al. |
| 2002/0065701 A1 | 5/2002 | Kim et al. |
| 2002/0128871 A1 | 9/2002 | Adamson et al. |
| 2002/0128890 A1 | 9/2002 | Dick et al. |
| 2002/0129031 A1 | 9/2002 | Lau et al. |
| 2002/0170035 A1 | 11/2002 | Casati et al. |
| 2003/0023593 A1 | 1/2003 | Schmidt |
| 2003/0023728 A1 | 1/2003 | Yaung |
| 2003/0045958 A1 | 3/2003 | Brandt et al. |
| 2003/0050800 A1 | 3/2003 | Brandt et al. |
| 2003/0074225 A1 | 4/2003 | Borsand et al. |
| 2003/0078813 A1 | 4/2003 | Haskell et al. |
| 2003/0149714 A1 | 8/2003 | Casati et al. |
| 2003/0158832 A1 | 8/2003 | Sijacic et al. |
| 2004/0015841 A1 | 1/2004 | Lepejian et al. |
| 2005/0027566 A1 | 2/2005 | Haskell |
| 2006/0184475 A1 | 8/2006 | Krishnan et al. |
| 2006/0184943 A1 | 8/2006 | Delmonego et al. |
| 2007/0130206 A1 | 6/2007 | Zhou et al. |
| 2009/0043634 A1 | 2/2009 | Tisdale |
| 2009/0089092 A1 | 4/2009 | Johnson et al. |
| 2010/0004948 A1 | 1/2010 | Toomey et al. |
| 2010/0131289 A1 | 5/2010 | Brandt et al. |
| 2011/0071850 A1 | 3/2011 | Nuthi |
| 2011/0320187 A1 | 12/2011 | Motik et al. |
| 2012/0041910 A1 | 2/2012 | Ludik et al. |
| 2012/0239671 A1 | 9/2012 | Chaudhri et al. |
| 2012/0245948 A1 | 9/2012 | Nolte et al. |
| 2012/0253836 A1 | 10/2012 | Nolte et al. |
| 2013/0046558 A1 | 2/2013 | Landi et al. |
| 2013/0085977 A1 | 4/2013 | Junker |
| 2013/0204830 A1 | 8/2013 | Franke |
| 2014/0058748 A1 | 2/2014 | Ford et al. |
| 2014/0095203 A1 | 4/2014 | Anand et al. |
| 2014/0244300 A1 * | 8/2014 | Bess ...................... G06F 16/22 |
| | | 705/3 |
| 2015/0081326 A1 | 3/2015 | Krishnapuram et al. |
| 2015/0120327 A1 | 4/2015 | Compton et al. |
| 2015/0149362 A1 | 5/2015 | Baum et al. |
| 2015/0317311 A1 | 11/2015 | Cannon et al. |
| 2016/0350361 A1 * | 12/2016 | Chen .................. G06F 16/2365 |
| 2017/0109477 A1 | 4/2017 | Farooq et al. |
| 2017/0124269 A1 | 5/2017 | Mcnair et al. |
| 2017/0161439 A1 | 6/2017 | Raduchel et al. |
| 2017/0212748 A1 | 7/2017 | Agnew et al. |

(56) References Cited

U.S. PATENT DOCUMENTS

| | | | |
|---|---|---|---|
| 2018/0181644 A1* | 6/2018 | Lyons | G06F 16/381 |
| 2019/0197421 A1 | 6/2019 | Agassi et al. | |
| 2019/0197428 A1 | 6/2019 | Kodish-Wachs et al. | |
| 2019/0303371 A1* | 10/2019 | Rowe | G06F 16/24564 |
| 2020/0342991 A1* | 10/2020 | Hu | G16H 70/00 |

FOREIGN PATENT DOCUMENTS

| | | | |
|---|---|---|---|
| EP | 1065618 | A2 | 1/2001 |
| EP | 1304645 | A2 | 4/2003 |
| JP | 2001-202408 | A | 7/2001 |
| WO | 99/24927 | A1 | 5/1999 |
| WO | 00/03344 | A1 | 1/2000 |
| WO | 00/14618 | A2 | 3/2000 |
| WO | 00/33238 | A3 | 11/2000 |
| WO | 2017/188987 | A2 | 11/2017 |

OTHER PUBLICATIONS

Apelon Products, Retrieved from internet URL: http://apelon.com/products/products . . . authoring.htm, May 22, 2002, 45 pages.

Health Supplier, Retrieved from internet URL http://www.healthtrade.com/tw/en/left/healthsupplier-en.htm, 2000, 4 pages.

Healthcare informatics: Feb. 1999 News and Trends, Retrieved from internet URL: <http://www.healthcare-informatics.com/issues/1999/02_99/news.htm>, printed on, May 22, 2002, pp. 1-12.

Organization Profile (OP FORM), Retrieved from the internet URL http://www.unece.org/ceiproj/exlop.htm, 2002, 3 pages.

OWL, an ontology language, Ontogenesis, available at: <http://ontogenesis.knowledgeblog.org/55>, Jan. 21, 2010, pp. 1-6.

Pre-Interview First Office action received for U.S. Appl. No. 16/233,348, dated Apr. 7, 2021, 4 pages.

Signature Product description information, Jun. 1985, 4 pages.

Batch, Kim, "Who Needs a Standard Medical Terminology.", Kim Batch Enterprise Architect Center for Biomedical Information, University of Pittsburgh., 9 pages.

Bechhofer et al., "Terminologies and terminology servers for information environments", Software Technology and Engineering Practice, 1997. Proceedings., Eighth IEEE International Workshop on [incorporating Computer Aided Software Engineering]. IEEE, 1997, Jul. 14, 1997, pp. 484-497.

Bertino et al., "A Flexible Model Supporting the Specification and Enforcement of Role-Based Authorization in Workflow Management Systems", Proceedings of the second ACM workshop on Role-based access, 1997, 12 pages.

Chun et al., "Dynamic Composition of Workflows for Customized eGovernment Service Delivery", Proceedings of the 2002 Annual National Conference on Digital Government Research, May 2002, pp. 1-7.

Dewan et al., "Workflow Optimization Through Task Redesign in Business Information Processes", Proceedings of the Thirty-First Hawaii International Conference on System Sciences, vol. 1, Jan. 1998, 13 pages.

Elkin et al., "Automated enhancement of description logic-defined terminologies to facilitate mapping to ICD9-CM", Journal of Biomedical Informatics Academic Press USA, vol. 35: 5-6, Oct. 2002, pp. 281-288.

Georgakopoulos et al., "An Overview of Workflow Management: From Process Modeling to Workflow Automatior Infrastructure", Distributed and Parallel Databases, vol. 3, No. 2, Apr. 1995, pp. 119-153.

Hogarth et al., "Terminology Query Language: A Server Interface For Concept-Oriented Terminology Systems", Proceedings of the AMIA Symposium American Medical Informatics Association., 2000, 5 pages.

Horrocks, Ian, "Description Logic: Axioms and Rules", Dagstuhl Rule Markup Techniques, Feb. 7, 2002, pp. 1-51.

Ingenerf et al., "Standardized terminological services enabling semantic interoperability between distributed and heterogeneous systems", International Journal of Medicine Informatics, 2001, pp. 223-240.

Lowe et al., "The image engine HPCC project. A medical digital library system using agent-based technology to create an integrated view of the electronic medical record.", Digital Libraries, 1996. ADL'96., Proceedings of the Third Forum on Research and Technology Advances in. IEEE, 1996, May 13, 1996, pp. 45-56.

Marazakis et al., "Management of Work Sessions in Dynamic Open Environments", Proceedings Ninth International Workshop on Database and Expert Systems Applications, IEEE, Aug. 26-28, 1998, 6 pages.

Nielsen et al., "Using Domino Workflow.", IBM Corporation, International Technical Support Organization, May 2000, pp. 148-178.

Nikolai et al., "Thesaurus federations: a framework for the flexible integration of heterogeneous, autonomous thesauri", Research and Technology Advances in Digital Libraries, 1998. ADL 98, Proceedings. IEEE International Forum on. IEEE, 1998, Apr. 22, 1998, pp. 46-55.

Noy et al., "Ontology Development 101: A Guide to Creating Your First Ontology", Web Page<(https://protege.stanford.edu/publications/ontology_development/ontology101.pdf>, Jul. 23, 2001, , retrieved from Internet Archive Wayback Machine <https://web.archive.org/web/20010801000000*/https://protege.stanford.edu/publications/ontology_development/ontology101.pdf> on Dec. 19, 2018, Dec. 19, 2018, pp. 1-20.

Raths, David, "The Importance of Bringing EMS Systems Into the HIE Loop", Healthcare Informatics, Health It Summit Series., May 31, 2017, 3 Pages.

Rector et al., "A Terminology Server for Medical Language and Medical Information Systems", Published in the Proceedings IMIA WG6, Geneva, May 1994, May 1994, pp. 147-157.

Taentzer et al., "Towards Refactoring of Rule-based, in-place Model Transformation Systems Taken", Available online at: <https://dl.acm.org/doi/10.1145/2432497.2432506>, 2021, pp. 41-46.

Yu et al., "Representing genomic knowledge in the UMLS semantic network", Proceedings of AMIA Annual Symposium the Emergence of Internetable Health Care Systems That Really Work, Nov. 6, 1999, pp. 181-185.

Zhao et al., "Temporal Workflow Management in a Claim Handling System", ACM SIGSOFT Software Engineering Notes, vol. 24, No. 2, 1999, pp. 187-195.

Non-Final Office Action received for U.S. Appl. No. 16/233,348, dated Oct. 26, 2022, 27 pages.

First Action Interview Office Action received for U.S. Appl. No. 16/233,341, dated Sep. 2, 2022, 18 pages.

Preinterview First Office Action received for U.S. Appl. No. 16/233,341, dated Jul. 22, 2022, 4 pages.

* cited by examiner

CONCEPT AGNOSTIC RECONCILATION AND PRIORITIZATION BASED ON DETERMINISTIC AND CONSERVATIVE WEIGHT METHODS

BACKGROUND

Today's world is increasingly dependent on storing massive amounts of data. Big data in healthcare is an issue due to the abundant health data that is amassed from numerous sources including separate electronic health record (EHR) systems, EHRs, outpatient facilities, imaging facilities, databases, wearable devices, public records, patient portals, clinical studies, and the like. Health data is available in extraordinarily high volumes. Additionally, due to the numerous sources involved in the care of individuals, content of the sources is often times highly variable in structure. Furthermore, communication across the numerous sources is necessary to provide continuity of care for individuals.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description.

In brief and at a high level, this disclosure describes, among other things, methods, systems, and computer-readable media for reconciling records from disparate sources and identifying relevant data to write to a system.

In one embodiment, a computerized method is provided. The method comprises receiving a plurality of records from one or more sources disparate from a first source; receiving at least one source record from the first source; calculating a probability of duplication for the plurality of records utilizing one or more rules; generating a first collection of records, wherein a collection of records includes records having a probability of duplication exceeding a predetermined threshold; weighting each record of the first collection of records with a weight value; identifying a highest-weighted record within the first collection, wherein the highest-weighted record is a record having a highest numerical weight value; generating a highest-weight collection, including at least the highest-weighted record within the first collection; analyzing the highest-weight collection against the at least one source record from the first source; and generating an updated set of records to write to the first source.

In another embodiment, one or more non-transitory computer-readable storage media are provided for storing computer instructions thereon for execution by one or more processors to perform a method. The method comprises receiving a plurality of records from one or more sources disparate from a first source; receiving at least one source record from the first source; calculating a probability of duplication for the plurality of records utilizing one or more rules; generating a first collection of records, wherein a collection of records includes records having a probability of duplication exceeding a predetermined threshold; weighting each record of the first collection of records with a weight value; identifying a highest-weighted record within the first collection, wherein the highest-weighted record is a record having a highest numerical weight value; generating a highest-weight collection, including at least the highest-weighted record within the first collection; analyzing the highest-weight collection against the at least one source record from the first source; and generating an updated set of records to write to the first source.

In one embodiment, a computerized system is provided in an embodiment of the present invention. The system comprises one or more processors to receive a plurality of records from one or more sources disparate from a first source; receive at least one source record from the first source; calculate a probability of duplication for the plurality of records utilizing one or more rules; generate a first collection of records, wherein a collection of records includes records having a probability of duplication exceeding a predetermined threshold; weight each record of the first collection of records with a weight value; identify a highest-weighted record within the first collection, wherein the highest-weighted record is a record having a highest numerical weight value; generate a highest-weight collection, including at least the highest-weighted record within the first collection; analyze the highest-weight collection against the at least one source record from the first source; and generate an updated set of records to write to the first source.

BRIEF DESCRIPTION OF DRAWINGS

Illustrative embodiments of the present invention are described in detail below with reference to the attached drawing figures, and wherein.

DETAILED DESCRIPTION

Figure 1:
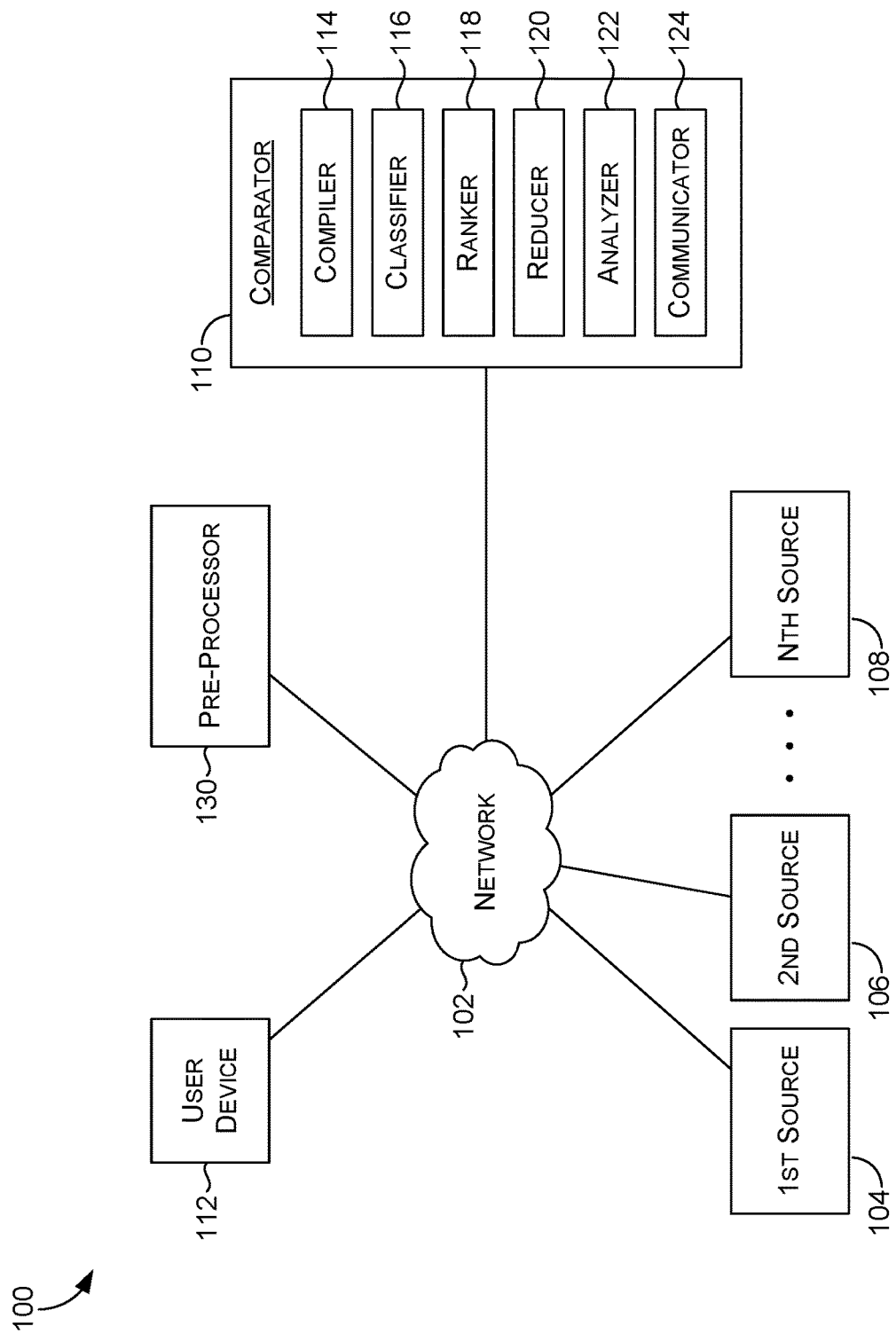
FIG. 1 depicts a block diagram of an exemplary system architecture in accordance with an embodiment of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described. Further, it will be apparent from this Detailed Description that the technological solutions disclosed herein are only a portion of those provided by the present invention. As such, the technological problems, solutions, advances, and improvements expressly referenced and explained should not be construed in a way that would limit the benefits and application of embodiments of the present invention.

Big data is a key feature of healthcare today. Providers need tools that enable them to provide continuity of care for individuals across several different providers (e.g., source systems of providers). Different systems inevitably use different standards or formats for their data. Thus, interoperability is a key priority for entities to ensure their systems can communicate with a variety of other systems that may utilize different standards and/or formats. Furthermore, communication across several different sources inevitably leads to duplication of records. For example, a primary care provider (PCP) may refer a patient to a specialist and, as a result, send the patient's records to the specialist. The specialist may already have the patient in the database from a previous referral and, thus, the specialist's system already has some of the same content from the records sent from the PCP. Duplication of records within multiple systems merely generates even more content to store and track across systems and leads to additional duplications when duplicates themselves are communicated from the same source (e.g., the specialist refers the patient on to a surgeon and sends their records and the PCP's records so that the communicated records include duplicates before even arriving at the system of the surgeon).

In order for a computerized system to organize source records (i.e., those records already present in a source system) and received records (i.e., those records received from disparate systems) and understand the information stored in electronic records, the computerized system can apply rules to evaluate the selected records. A separate rule can be used to evaluate each possible combination of variables and values for each variable that may be present in the record.

At a high level, embodiments of the present invention utilize rules to reconcile information currently stored in one system (e.g., a source system) with information imported or received from a plurality of diverse systems, in order to generate accurate information sets that should be written to the source system. Reconciliation of records is only the beginning on tackling the issue though. Once reconciled or, in other words, once the duplicate records are identified, there is no way to know which record to keep and write to the system. The present invention provides both a reconciliation and ranking iterative process to provide, as output, a consolidated updated set of records to be written to the record, where the updated set of records is free of duplicate records (i.e., no duplicates are present) and includes one or more updated records (utilizing HTTP PATCH logic, for example) including the information from any duplicate records in a single record.

Referring to the drawings in general, an initially to FIG. 1, a block diagram illustrating an exemplary system 100 architecture in which some embodiments of the present disclosure may be employed is provided. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

It should be understood that the system 100 shown in FIG. 1 is an example of one suitable computing system architecture. Each of the components of FIG. 1 may be implemented via any type of computing device. The components can communicate with each other via a network including, without limitation, one or more local area networks (LANs) and/or wide area networks (WANs). Such networking environments are commonplace in offices, enterprise-wide computer networks, intranets, and the Internet. It should be understood that any number of components shown in FIG. 1 may be employed within the system 100 within the scope of the present invention. Each may be implemented via a single device or multiple devices cooperating in a distributed environment. Additionally, other components not shown may also be included within the environment.

Among other components not shown, the system 100 includes a variety of user devices, such as a first source 104, a second source 106, an n source 108, a comparator engine 110, a pre-processor 120, and a user device 112, any of which can interact with any other component of the system 100 and each of which are communicatively coupled with each other. These components may communicate with each other via networking means (e.g., network 102) which may include, without limitation, one or more local area networks LANs and/or wide area networks (WANs). In exemplary implementations, such networks comprise the Internet and/or cellular networks, amongst any of a variety of possible public and/or private networks.

User device 112 can comprise any type of computing device capable of use by a user. By way of example and not limitation, a user device can be embodied as a personal computer (PC), a laptop computer, a mobile device, a smartphone, a tablet computer, a smart watch, a wearable computer, a fitness tracker, a personal digital assistant (PDA) device, a global positioning system (GPS) device, a video player, a handheld communications device, an embedded system controller, a camera, a remote control, a consumer electronic device, a workstation, or any combination of these delineated devices, a combination of these devices, or any other suitable computer device.

The sources, shown in FIG. 1 as first source 104, second source 106, and n source 108 can be collectively referred to herein as sources 104-108. Sources 104-108 can be any system capable of storing, receiving, transmitting, or the like, records or any health-related data. Any one of the sources can be an electronic health record (EHR) server, a health information exchange (HIE), a patient portal, a government database, a pharmacy database, etc. The content available within the sources 104-108 can include records of treatment events, medication history, diagnoses, problems, allergies, demographic attributes, summary of episode notes (SOEN), CDA (Clinical document architecture) documents, laboratory tests and/or results, time and data information, images, clinical notes, appointment notes, emergency contact information, clinical documentation of any kind, and any other health-related data, or any combination thereof for a plurality of individuals. Sources 104-108 can be disparate sources or, in other words, may be associated with different entities (e.g., source 104 may be associated with a hospital in Pennsylvania while source 106 may be associated with a pharmacy in Florida unrelated to source 104). Each of the sources 104-108 can utilize different standards or formats within their databases (e.g., JSON, XML, YAML, HL7, CCDA, etc.). Furthermore, while sources 104-108 are described herein as single sources (e.g., single databases), sources 104-108 can be multiple data stores each associated with one or many different entities. One of skill in the art will understand the sources can take a variety of forms, be represented as multiple components, and communicate with any number of other sources.

The comparator engine 110 comprises instructions to perform iterative reconciliation and ranking processes, as described herein. In particular, and as described further herein, the comparator engine 110 can receive data from a plurality of disparate sources (e.g., sources 104-108) and perform iterative analyses to identify duplicates within the data. If duplicates are present, the comparator engine 110 includes instructions to weigh and rank the duplicative content such that the relevant content is written to the record appropriately and duplicate records are avoided. A duplicate, as used herein, refers generally to a record that is a copy of another record. In embodiments, a duplicate can be a record that has a probability/confidence level above a predetermined value to be a copy of another document. Comparator engine 110 can facilitate communication between the sources 104-108 and a plurality of other sources such as user device 112, a data store, and the like. The comparator engine 110 can include an application programming interface (API) library that includes specifications for routines, data structures, object classes, and variables that support the interaction of the comparator engine 110 architecture and the software framework of one or more disparate sources (e.g., sources 104-108). These APIs can include configuration specifications for the system 100 such that the components therein can communicate with each other, as described herein.

Initially, data from disparate sources can be received and pre-processed by a pre-processor 130, prior to communication to the comparator engine 110. The comparator 110 engine consumes data in a particular format. In embodiments, the comparator engine 100 consumes data in FHIR format. The data received from data sources 104, 106, and 108, can be in any format and needs to be transformed to FHIR format to be used by the comparator engine 110. To do this, the pre-processor 130 identifies one or more parameters of the received data. In embodiments, two parameters that can be identified are the coding system (e.g., RXNORM, CVX, etc.) and the type (e.g., codeable concept or free text).

The parameters are identified by the pre-processor 130 and grouped together to feed to the comparator engine 110. In particular, it is important to ensure that the comparator engine 110 is comparing like items and not items that are not related at all. The pre-processor 130 can identify "system+ codeable concept" or "system+free text" parameters in order to populate one or more groups of data to feed to the comparator engine 110. For example, different coding systems are used for different concepts: CVX is used to code vaccinations while RXNORM can be used to code medications. In processing an item, identification of the CVX system indicates an immunization concept. From that, either a codeable concept (e.g., numerical coding value: CVX 101) or free text (e.g., a textual name of the immunization: tetanus) can be identified. The "system+codeable concept" or "system+free text" parameters can be used to translate the data to FHIR-supported concepts. Put simply, if the coding system along with one or more of the codeable concept or free text is known, the information can be translated to FHIR standard. The translation can be done by the pre-processor 130, a separate translator service (not shown), a component of the comparator engine 110, or the like. The translation can be completed using a translation map that maps various text and codes for a plurality of coding systems to FHIR standard terminology.

Turning back to the comparator engine 110, to execute the instructions to perform iterative reconciliation and ranking the comparator engine 110 can include a compiler 114, a classifier 116, a ranker 118, a reducer 120, an analyzer 122, and a communicator 124.

Compiler 114 can perform an initial classification on data received at the comparator engine 110. Recall that the data received is from one or more disparate sources in embodiments. In other embodiments, the data is received from a single source.

Classifier 116 can perform an initial classification of a plurality of records based on one or more rules. A rule is a type of predicate that will return a floating point instead of a Boolean value (hence, probability). The one or more rules (also referred to herein as "rules") can assign a numerical value to an outcome of a rule and return a value between a min and max value. Data can be broken down into objects (e.g., encounters) and broken further down into fields (e.g., summary, problems, allergies, status, etc.). Each field can be used to isolate comparisons with knowledge of the values/ variables of the fields. Thus, the rules used herein all take the same form and are, therefore, data-driven rules. When looking at object fields and variables thereof, there are three possible outcomes from comparing this data in a rule: the fields are equal (variable match), the fields are not equal (variable mis-match), and the fields did not exist (null or non-existent variable). In the current comparator engine 110, values are assigned (e.g., x, y, z respectively) to each of the three possible outcomes. To illustrate the assignments of different numbers for the outcomes isEquals, isNull, and isDiffer, an example is provided below in JSON format for readability.

```
{
"mrn": "1234",
"patient": {
   "given": "Joseph",
   "family": "Smith"
}
},
{
"mrn": "1029",
"patient": {
   "given": "Joseph",
   "family": "Smith"
}
},
{
"patient": {
   "given": "Joe",
   "family": "Smith"
}
}
```

From the above, four data types can be derived:
1. mrn
2. patient
3. patient.given
4. patient.family These fields can be used in the comparator engine 110 and, more particularly, by the compiler 114 as data-driven rules once values are assigned to the outcomes. For the purposes of this example, assume that MRN (medical record number) is a universal identifier so that if it is equivalent on more than one record it can be said that the documents are 100% equivalent. Moving on to names, they have some bearing but not much. First names, for instance, encounter duplicates frequently. Last names do not encounter duplicates as often, but it is not uncommon either. So, if one were to rank the fields in order of importance for determining a duplicate, it could be:
1. mrn
2. patient
3. patient.family
4. patient.given A set of data-driven weights can be identified that can correspond to the desired importance of the fields within the rules. Put simply, a numerical value is assigned to each of isEqual, isNull, and isDiffer outcomes for each of the fields above. In another embodiment, rather than reasoning a desired outcome and associated values with fields, a system could ingest large amounts of data and observe how important each of these values was in the outcome and utilize a machine-algorithm to implement this pattern. A specific example is provided with reference to FIG. 2 and discussed hereinafter.

By utilizing the rules, the output will be a numerical value that corresponds to one of isNull, isEqual, or isDiffer outcomes after at least two objects have been processed for the desired fields. Take, for instance, a very simple case where only one rule is present:

| Name | isDiffer | isEqual | isNull |
|---|---|---|---|
| Patient.family | −20 | 10 | 5 |

Using the above, it is apparent that the min of this set is −20 and the max is 10. The output from this rules engine (i.e., the comparator engine 110) is a probability—how probable is it that two entities are duplicates? Using the above example and the rule, it can be identified that the variables for the field "patient.family" are the same (i.e., both have the last name Smith). The rule above would output 10 (Result, in the below equation) since the variables are equal. To get a probability from this the following is utilized:

Probability=(Result−min)/(max−min)

Probability=(10−−20)/(10−−20)

Probability=1 or 100%

In the event multiple rules are utilized, a min and a max for each set needs to be identified, which is the summation of the min's of each rule and the summation of the max's of each rule. To illustrate, an example is provided below:

| Search Group | Variable | isEqual | isDiffer | isNull |
|---|---|---|---|---|
| 1 | Encounter.id | 100 | −5 | 0 |
| 2 | Encounter.period.end | 3 | 5 | −4.32 |
| 1 | Encounter.status | 2 | 4 | 6 |

The values assigned to the variable Encounter.id are 100, −5, and 0. Thus, the min for this set is −5 and the max is 100. The same is done for the other two variables: the values assigned to the variable Encounter.period.end are 3, 5, and −4.32 so the min is −4.32 and the max is 5; the values assigned to the variable Encounter.status are 2, 4, and 6 so the min is 2 and the max is 6. Rules are calculated in order so the first group (identified above as search group 1) will go first (i.e., Rules 1 and 3).

The rules are assembled so the calculation can proceed using the below equation:

$$R = \left( \frac{(\sum W_{result} - \sum W_{min})}{(\sum W_{max} - \sum W_{min})} \right)$$

$W_{min}$ is the sum of the min mentioned above for rules 1 and 3: −5, +2=−3
$W_{max}$ is the sum of the max mentioned above for rules 1 and 3: 100+6=106
$W_{result}$ is determined by the output of the rules, it is known that $W_{max} \geq W_{result} \geq W_{min}$ and it is known from rule assembly that the value can only be one of the outcomes for the rule. Assume the outputs are:
Rule 1: isEqual=100
Rule 3: isEqual=2
Therefore, $W_{result}$ is given by the above min's mentioned above, therefore $W_{result}$=100+2=102.

The values are then inserted in the above-given equation.

Group 1 Result=(102−−3)/(106−−3)=(105/109)= 0.9633.

The result (i.e., 96%) is then compared to a predetermined threshold for determining a duplicate. Assume the threshold in this example is 0.75. 0.96>0.75 so it is determined by classified 116 that this is a duplicate. The same is performed for Search group 2 above and the below result is achieved: R=(3−−4.32)/(5−−4.32)=(7.32/932)=0.7854. This, also is deemed a duplicate as it is greater than the predetermined threshold of 0.75 in this example.

Figure 3:
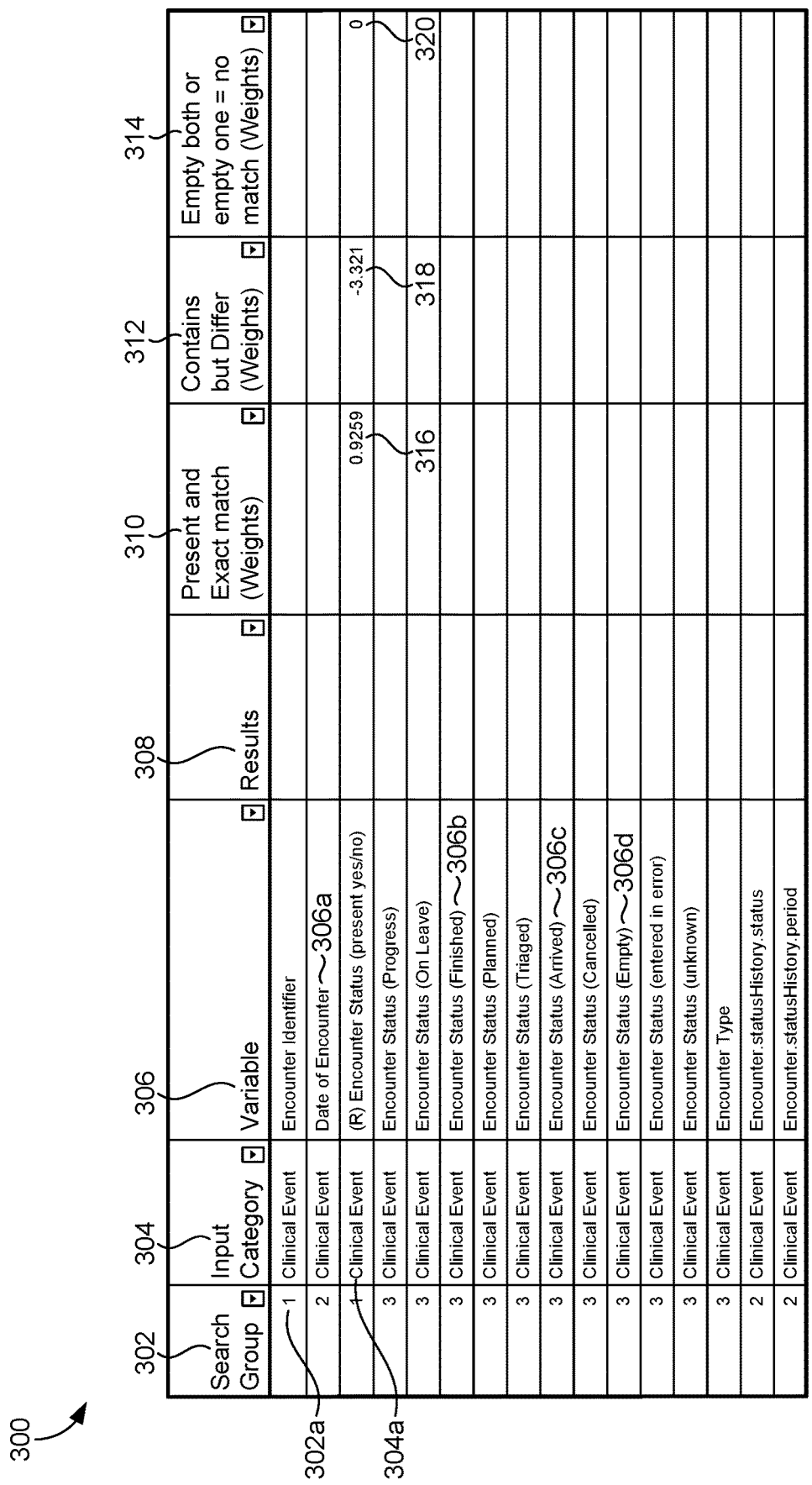
FIG. 3 depicts an exemplary screen shot illustrating an exemplary hash map in accordance with an embodiment of the present invention.
Figure 4:
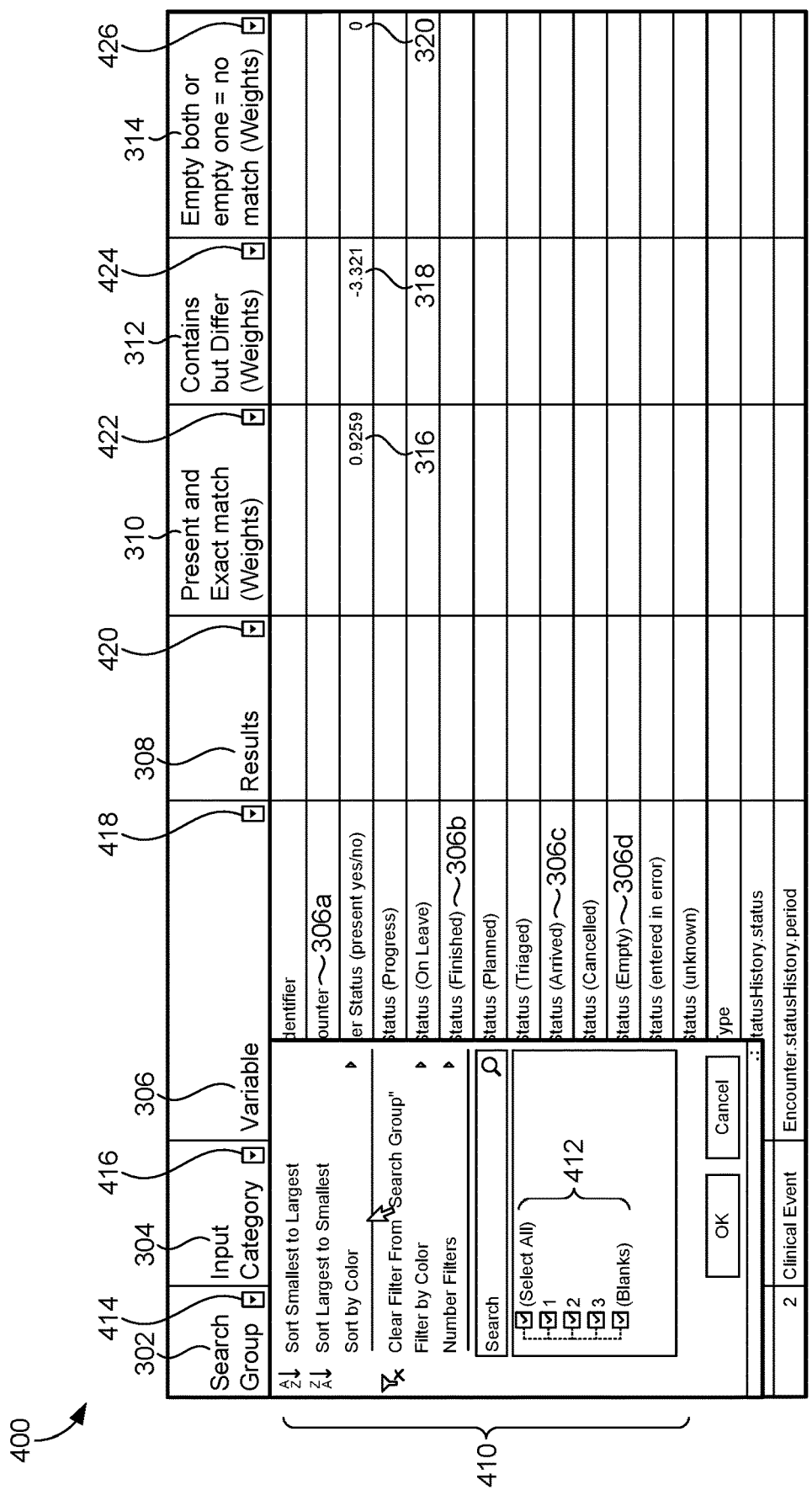
FIG. 4 depicts an exemplary screen shot illustrating a search function within an exemplary hash map in accordance with an embodiment of the present invention.

A hash map of values (as shown in FIG. 3) can be returned illustrating each search group, each variable, outcomes for each variables, and results for each group. The hash map can be searched by search box 410, as illustrated in FIG. 4, and filtered by search groups 412 or any other desired criteria by selection of filter selectors 414, 416, 418, 420, 422, 424, and 426.

As shown in FIG. 3, search groups 302 such as search group 302*a* can be associated with each input category 304 and/or variable 306. A results portion 308, an isEqual weight portion 310, an isDiffer weight portion 312, and a null portion 314 are also provided. As shown, several variables are provided as variables 306*a*, 306*b*, 306*c*, and 306*d*. Weights can be provided, such as values 316, 318, and 320, in the respective weight portions. Also shown is the results portion 308 where a duplication result or probability can be provided.

Returning now to the example, in addition to the use of rules, cascading filters can also be utilized so that groups of rules can be processed in a specified order. Once a rule-group has been evaluated, a probability is returned. If the probability does not meet a predetermined threshold, the process can stop. This cascading reduces the processing power needed when working with abstractly large data. Specifically, the cascading filters allow for processing of a data set to stop when it is apparent from the first filter that a threshold is not met and, thus, eliminates the need for further processing on that data set.

Once the probability/confidence level of duplication is identified, the classifier 116 can generate a collection of records according to the probability of duplication. Thus, the classifier 116 outputs one or more collection of records that includes one or more records therein identified to have a probability of duplication exceeding a predetermined threshold.

Now that the classifier 116 has classified each record into the appropriate group and identified a probability of duplication for each record and/or group, the collection of records are communicated to the ranker 118. To put simply, the goal of the previous steps was to identify equal items or duplicate of one another. The goal of the steps to follow is to rank equal items in order to identify the best or most appropriate item of the duplicate items to write to a record (e.g., EHR) or system. The ranker 118 can rank duplicates only. If items are not duplicate of any other record according to the rules, no ranking is necessary as that item will be written to the system. No further processing is needed for items that are not duplicates. Typically, because of the way java stores sets, this selection has the possibility of being completely random. The ranking described herein is necessary to ensure correct data is written to the system.

The ranker 118 can utilize a set of rankings to assign a weight value to one or more variables of an item. The variables to which weight values are assigned can be the same of different than the variables that are evaluated in the one or more rules utilized by the classifier 116. By way of example only, assume that for the variable Encounter.status discussed above, a weight value of 5 can be given for a status of finished while a weight value of 2 can be given for a status of preadmit. Thus, an Encounter.status of finished will be weighted higher than that of a status of preadmit.

The ranker 118 can associate a weight value to each individual record within each collection of records. If a collection of records includes only a single record, a weight value is not necessary as the single record in the collection will be ultimately written to the system. The ranker 118 can then evaluate each collection of records individually to identify, within each collection, a highest-weighted record. The highest-weighted record for each collection can then be, by the reducer 120, compiled into a reduced record set comprising the highest-weighted record from each collection evaluated by the ranker 118. Alternatively, the ranker 118 can rank each record within the collection of records and communicate that information to the reducer 120 to then be reduced to a reduced set (i.e., the reducer 120 can identify the highest-weighted record within each collection).

The reduced set can then be evaluated by an analyzer 122. The analyzer 122 can analyze the reduced set of records against an original source input. The original source input can be an original source record from a first source, a plurality of source records from the first source, an entire database of records from a first source, or the like. The analyzer 122 can perform duplication analysis on each of the records (e.g., the source record and each record in the reduced set) but that is not necessary since the analyzer 122 already knows the outputs of the probability of duplication for each combination of records from the classifier 116. Either scenario, however, is contemplated in embodiments herein. Any records that are not duplicates of another record can be extracted from the analyzer 122 for further transmission by the comparator engine 110 and no further processing is needed. In embodiments, the records that are not duplicated of any other record are compiled to an "Add" record set to be added to the record or system to which the records are written. Any records that are identified as duplicates by the analyzer 122 can be compiled into an "Update" set or records. The "update" set of records can include information from both records that are duplicates or contain the information of the highest-weighted record of the duplicates. The duplicate records can be updated using HTTP Patch logic such that a value is changed or updated in one of the records. Various rules can be created to identify which record should proceed to be written to the system and, thus, have changes made to it. For instance, a most recent record according to time stamps can be used and any discrepancies in the source record evaluated against a time stamp linear review (e.g., preadmit comes before discharge so a status wouldn't be updated from discharge to preadmit). For non-linear variables, various other rules can be implemented to identify a best record (e.g., incoming records take priority over pre-existing records, etc.). This can be automatically implemented by the system or queued for further user review prior to writing the records to the system. Once the analyzer 122 has identified the records to write to the system, a communicator 124 can communicate a final set to the system to which the records should be written.

Figure 2:
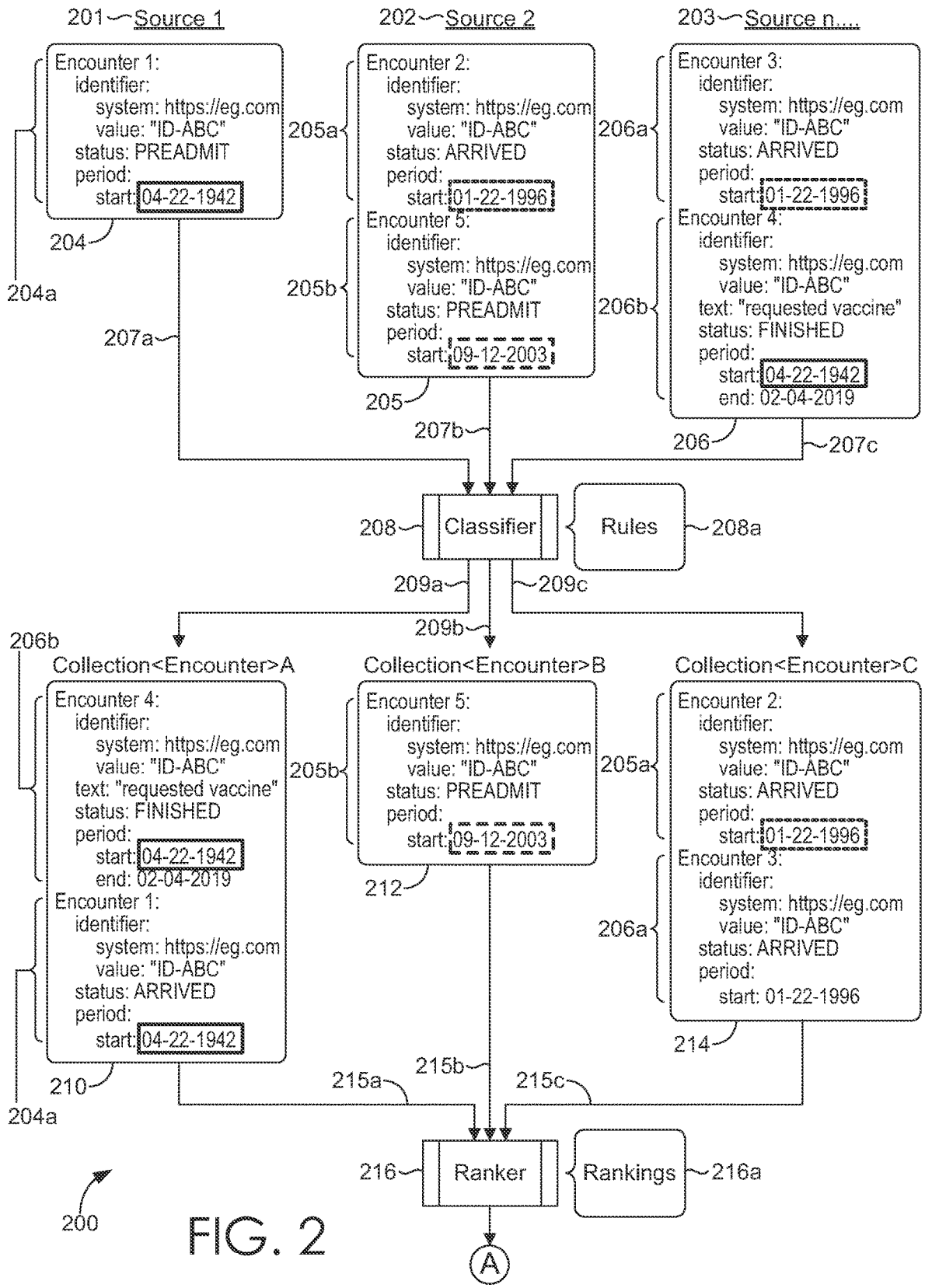
FIG. 2 depicts a diagram of exemplary component interactions in accordance with an embodiment of the present invention.
Figure 2:
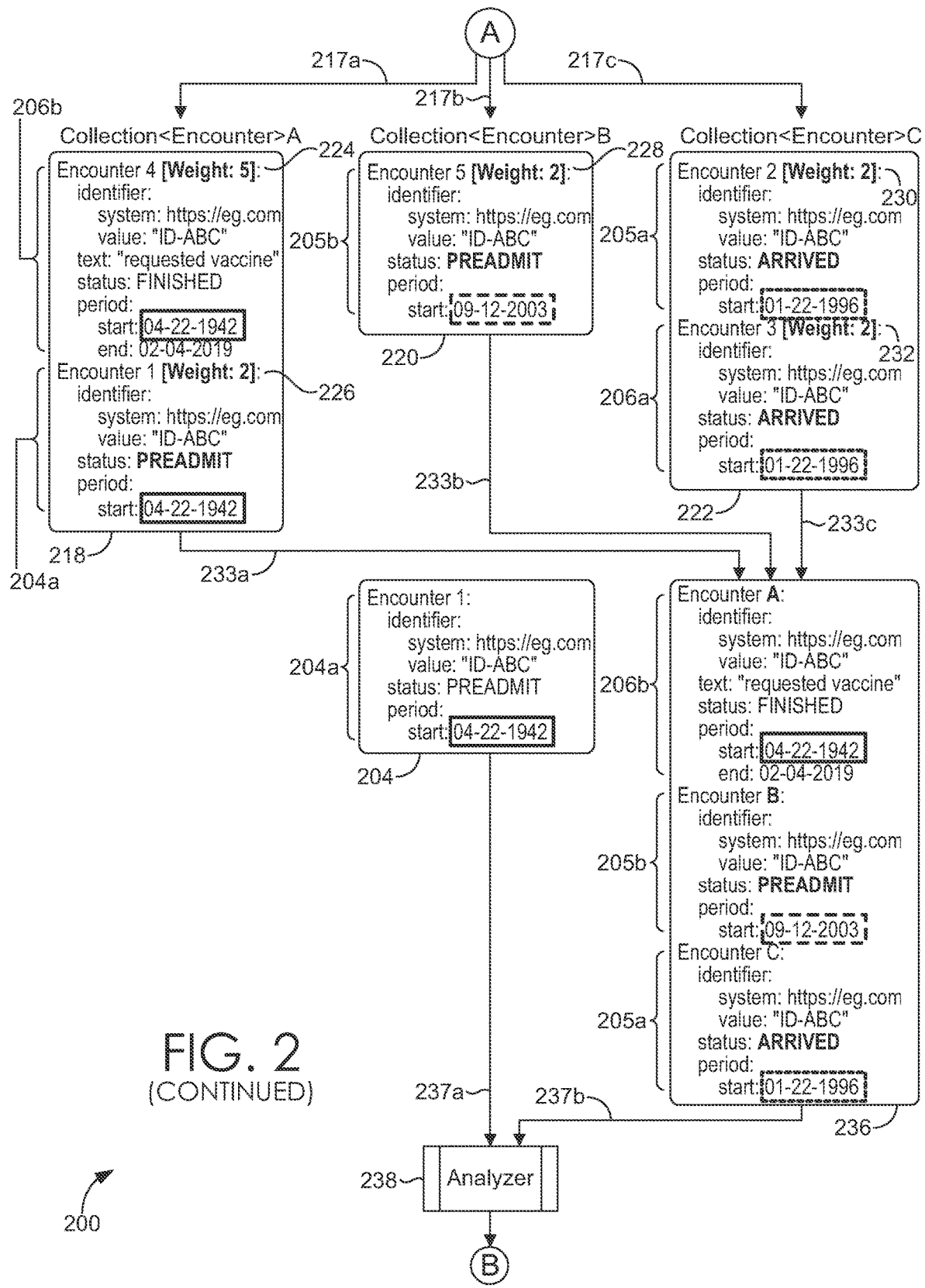
Figure 2:
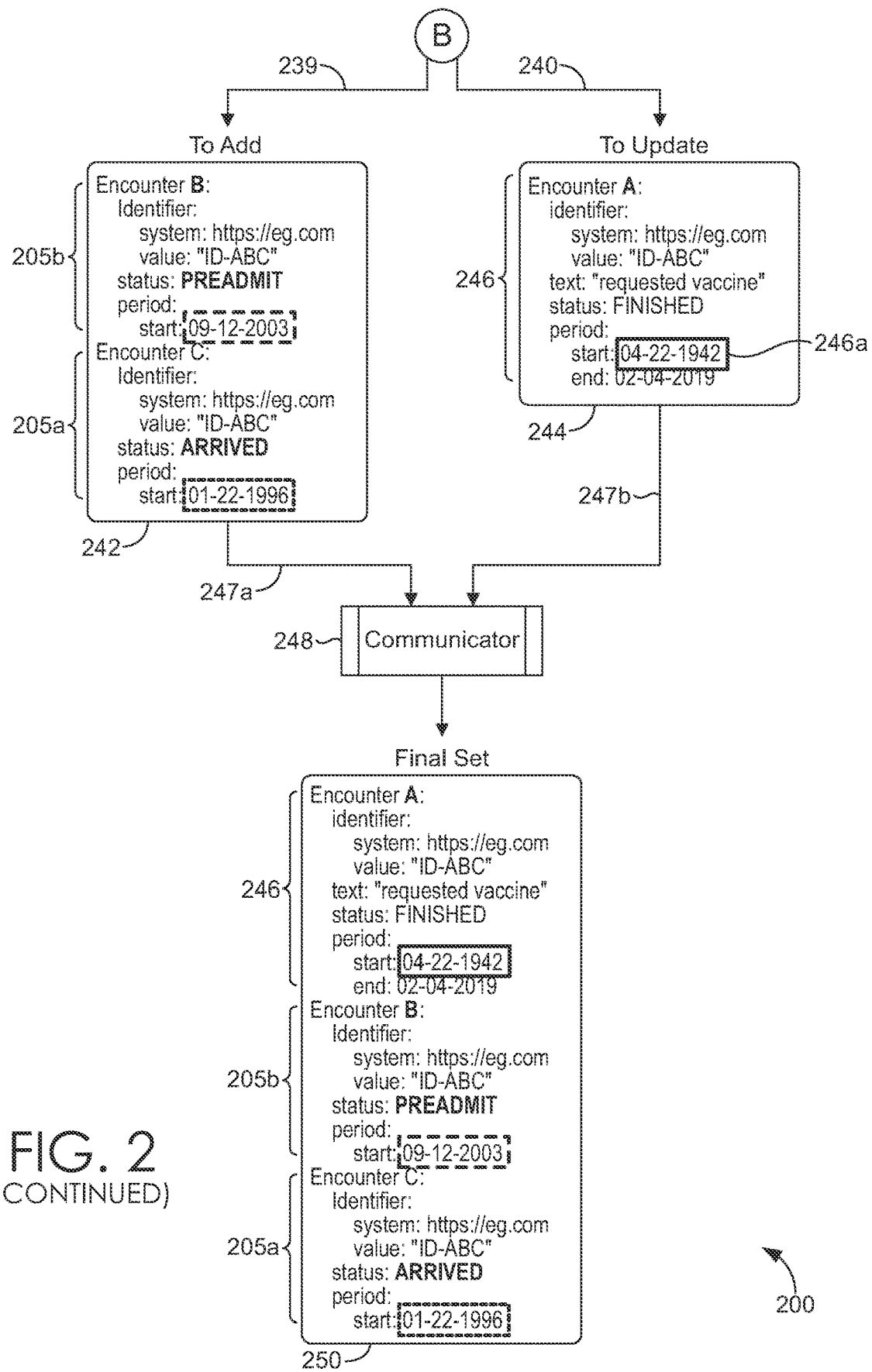

Having described the components of system 100, exemplary component interactions of the components of FIG. 1 are now described with reference to the flow provided in FIG. 2. In application, FIG. 2 can be referenced to illustrate the method 200 described as being performed by the system 100 of FIG. 1. As explained, data (shown as data 204, data 205, and data 206) can be received from a plurality of sources (shown as source 1 201, source 2 202, and source n 203). As is also shown, each data item can include one or more records within. For instance, data item 204 includes record 204a; data item 205 includes record 205a and record 205b; and data item 206 includes record 206a and record 206b. For the purposes of this example, assume that record 204a is the original source record from source 1 201, to which resulting records should be written. Each received source can be communicated (by, for example, the compiler 114 of FIG. 1 and not shown here) to the classifier 208 via transmission 207a, 207b, and 207c.

The classified 208 can include one or more rules 208a to apply to one or more variables of each record received and, in turn, classify each record into a collection of records based on the probability of duplication. To illustrate this example, assume the following rules:

| Variable | isEqual | isDiffer | isNull |
|---|---|---|---|
| Identifier | 1 | −1 | 0 |
| Period.Start | 1 | −2 | −2 |

Initially, a min and max for each rule is identified. For the identifier variable rule set, the min is −1 and the max is 1. For the period.start variable rule set, the min is −2 and the max is 1. Thus, the sum of the min (i.e., absolute min) is −1+−2=−3 and the sum of the max (absolute max) is 1+1=2. This can be used to identify the probability of duplication or confidence level of duplication for each of the records. Take, for instance, record 205a and record 205b. Both record 205a and 205b have an identifier of "ID-ABC" while record 205a has a period.start of 1-22-1995 and record 205b has a period.start of 9-12-2003. Thus, the identifier variable is the same (1) but the period.start variable is different (−2) according to the above rules. Thus, the result of records 205a and 205b is R=identifier value+period.start value=1+−2=−1. The probability/confidence level of duplication can be evaluated using the below:

Probability/confidence level of duplication=(R−min)/(max−min)

(−1−−3)/(2−−3)

2/5=0.4=40%

The probability/confidence level of duplication is then compared to a predetermined threshold to identify if the records are duplicates of one another. Assume, in this example, the predetermined threshold is 0.9 or 90%. Thus, records 205a and 205b are determined, by the classifier 208 to not be duplicates of one another. Thus, records 205a and 205b will not end up in the same collection of records generated by the classifier 208. The predetermined threshold can be configurable.

By way of further example, records 206a and 206b can be evaluated in the same fashion. Records 206a and 206b both have the identifier as "ID-ABC" so the value for that rule is 1 since they are equal. Record 206a has 1-22-1996 as the period.start while record 206 has 4-22-1942. Thus, the value for the period.start rule is −2 since they are different. Thus, the result is −+−2=−1. We know from the above example evaluated records 205a and 205b that with R=−1, the probability of duplication is 0.4 or 40% so the classifier 208 can identify that records 206a and 206b are not duplicates of one another.

Continuing on with another example, record 205a and record 206a both have an identifier of "ID-ABC" and a period.start of 1-22-1995. Thus, the value of the identifier rule set is 1 since they are equal and, similarly, the value of the period.start rule set is 1 since they are equal. Thus, R=1+1=2. The probability/confidence level of duplication is calculated for records 205a and 206a as follows:

Probability/confidence level of duplication=(R−min)/(max−min)

(2−−3)/2−−3)

5/5=1=100%

100% exceeds the threshold of 0.9 or 90%. Thus, classifier 208 can determine that records 205a and 206a are duplicates. As they are identified as duplicates, records 205a and 206a are included in the same collection of records 214.

Classifier 208 continues on with calculating the probability of duplication for each of the records received until each are categorized into a collection of records. A collection of records includes one or more records each having a probability of duplication to one another that exceeds the predetermined threshold. As is shown, records 205a and 206a had a probability/confidence level of duplication of 100% and are both included in collection 214. The collection of records 210, 212, and 214 created at steps 209a, 209b, and 209c. The collections 210, 212, and 214 are then transmitted at transmissions 215a, 215b, and 215c to the ranker 216.

In embodiments, the confidence level of duplication is used to determine whether to send records on to the ranker 216 or to stop the process (not shown). One or more rules can be built into the engine to stop the process from further evaluation when a predetermined number of identifiers that are matches is below a predetermined threshold or when a confidence level of duplication is 0%. For example, if zero of three variables match, no further analysis may be needed as the records are not duplicates and, thus, the method may stop without communicating the records on to the ranker 216.

The ranker 216 can include one or more set of rankings 216a. The set of rankings 216a can include a weight value for one or more variables. The one or more variables for which a weight value is provided can be the same, different, or a combination thereof of the variables evaluated in the one or more rules of rules 208a. In this example, assume the following rankings: Field: status

ARRIVED: 2
FINISHED: 5
UNKNOWN: −1
PREADMIT: 2
NULL: −1

Each record in the collections 210, 212, and 214 can be ranked or weighted based on the set of rankings to create a weighted collection shown at weighted collections 218, 220, and 222. As can be seen, record 206b has a weight value 224 of 5 since the status is FINISHED; record 204a has a weight value 226 or 2 as the status is PREADMIT; record 205b has a weight value 228 of 2 since the status is PREADMIT (note that this record does not need to be weighted at all since it is the only record in collection 220); record 205a has a weight value 230 of 2 as the status is ARRIVED; and record 206a has a weight value of 232 as the status is ARRIVED. At this point, a highest-weighted record in each collection can be identified and communicated at transmissions 233a, 233b, and 233c as a reduced set 236. The reduced set 236 includes each of the highest-weighted records from each of collection 218, 220, and 222. Thus, record 206b from collection 218 (since weight 5 is greater than weight 2 for record 204a), record 205b from collection 220 (as it is the only record in the collection, and either record 205a or record 206a from collection 222 since their weight values are equivalent. In the case where weight values are equivalent, additional rules/ranking sets can be included to further filter the records (e.g., a most recent record can be weighted higher, an author of the record can be identified an weighted, a source organization can be identified, and the like). In this example, for clarity, assume that record 205a was documented by a treating clinician while record 206a was edited by billing personnel so record 205a is selected.

At this point, each of the reduced set 236 and the source record 204 are communicated at steps 237a and 237b to the analyzer 238. The analyzer 238 can evaluate the reduced set 236 against the source record 204. The analyzer 238 can identify a confidence level of duplication for each record in the reduced set 236 against the source record 204 from the classifier 208. Thus, no additional probability of duplication is needed. From this, the analyzer 238 knows that record 206b and record 204a were identified as being duplicates by the classifier 208 and, thus, were included in collection 218 together. Thus, the analyzer 238 is further aware that records 205b and 205a of reduced set 236 are not duplicates of record 204a and the non-duplicates can be compiled by the analyzer 238 at step 239 into an "add" set 242. An "add" set includes one or more records that are determined to not be duplicates of any other record and were the highest-weighted records in their collections. As is shown, add set 242 includes both records 205b and 205a.

The analyzer 238 further analyzes source record 204a against duplicate record 206b to determine which to write to the system. Now, according to the set of rankings 216a, record 206b was ranked higher than record 204a in collection 218. If for instance, record 206b had been ranked lower, record 204a would have been the highest-weighted record in collection 218 and would have been passed on to the reduced set 236 and compared against itself. No change would have been identified so record 204a could be written to the record as-is. However, record 206b, in this example, was ranked higher than record 204a. Thus, the analyzer 238 can identify it was the higher-weighted record and identify any differences between record 206b and record 204a. Here, the status of record 204a is PREADMIT while the status of record 206b is FINISHED. As previously discussed, status can be a linear variable such that it is relatively easy for the analyzer 238 to identify which is most recent. Furthermore, for non-linear variables time stamps can be utilized by the analyzer 238 to determine which record should be written to the system. In this case, it is clear that record 206b is the most recent of the duplicates and should be selected to be written to the system. Thus, the analyzer 238 creates an "update" set 244 at step 240 that includes an updated record 246. The updated record can be created using HTTP Patch logic such that values are changed within the record. Thus, record 204a can be updated to include a FINISHED status and any additional information from record 206b. Alternatively, the updated record 246 can be the selected record 206b plus any additional information from the source record 204a that is not included in the selected record. In other words, the duplicate of the source record 204a can be updated with content of the source record.

The "add" set 242 and the update set 244 are communicated at steps 247a and 247b to the communicator 248. The communicator 248 creates an aggregated set 250 (or final set) to be communicated on to a system to which the records are to be written. As shown, the aggregated set 250 includes each record from the "add" set 242 and the update set 244 (i.e., records 205b, 205a, and 246).

Figure 5:
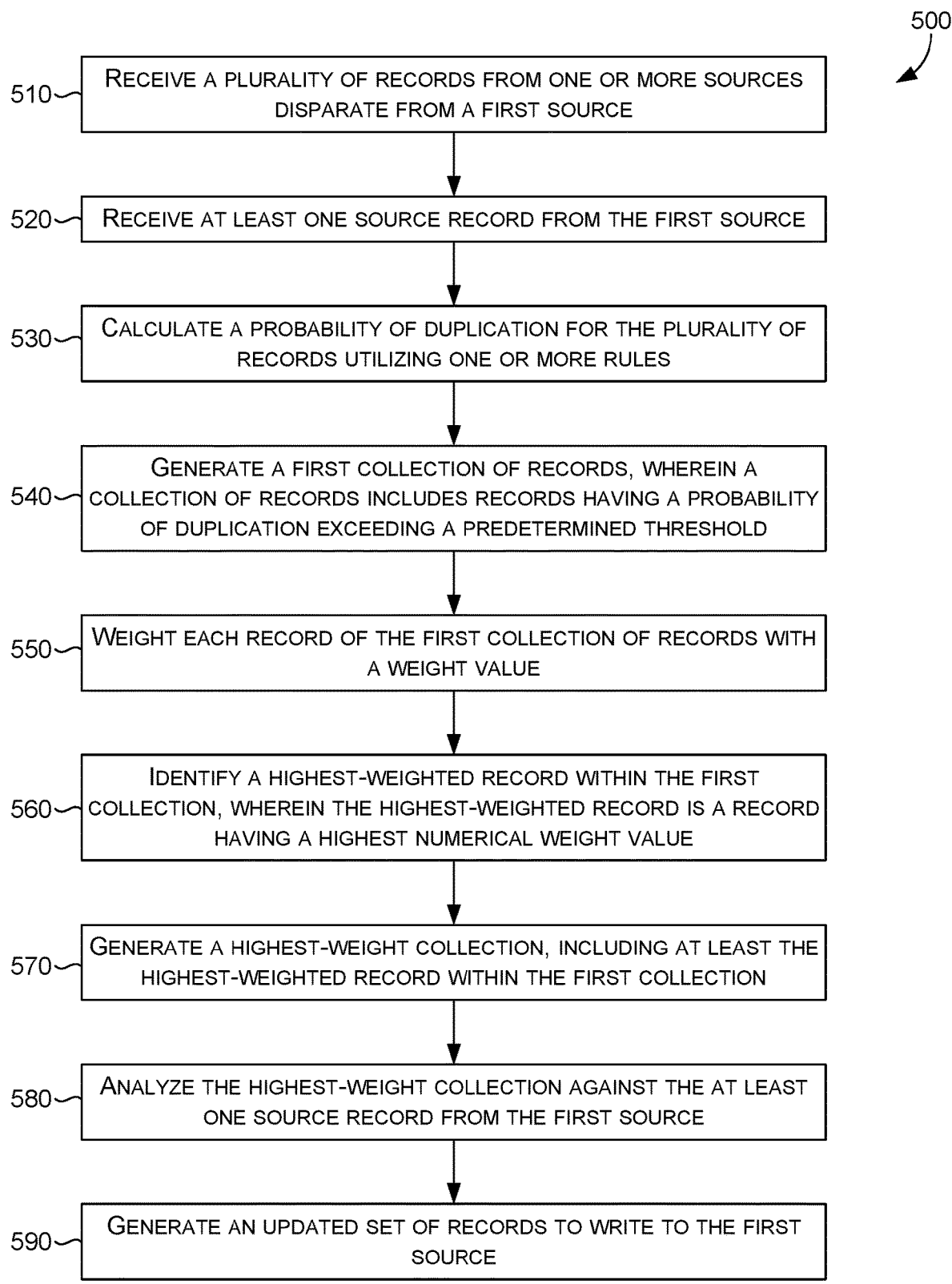
FIG. 5 depicts a flow diagram of an exemplary method in accordance with an embodiment of the present invention.

Turning now to FIG. 5, an exemplary method 500 in accordance with embodiments of the present invention is provided. Initially, at block 510, a plurality of records is received from one or more sources disparate from a first source. The sources can be EHR servers and the like, where the EHR servers are associated with different entities. At block 520, at least one source record is received from the first source. At block 530, a probability of duplication for the plurality of records is calculated utilizing one or more rules. The one or more rules provide values for each outcome of one or more variables. From that, at block 540, a first collection of records is generated. A collection of records includes records having a probability of duplication exceeding a predetermined threshold. A predetermined threshold can be a configurable value and can be represented as a percentage value. Each record of the first collection of records is weighted with a weight value at block 550. Using the weight values, a highest-weighted record is identified within the first collection at block 560. The highest weighted record is a record having a highest numerical weight value. At block 570, a highest-weight collection is generated that includes at least the highest-weighted record within the first collection. If more than the first collection is present, the highest-weight collection can include the highest-weighted record from each additional collection present. At block 580, the highest-weight collection is analyzed against the at least one source record from the first source. An updated set of records is generated to write to the first source at block 590.

Figure 6:
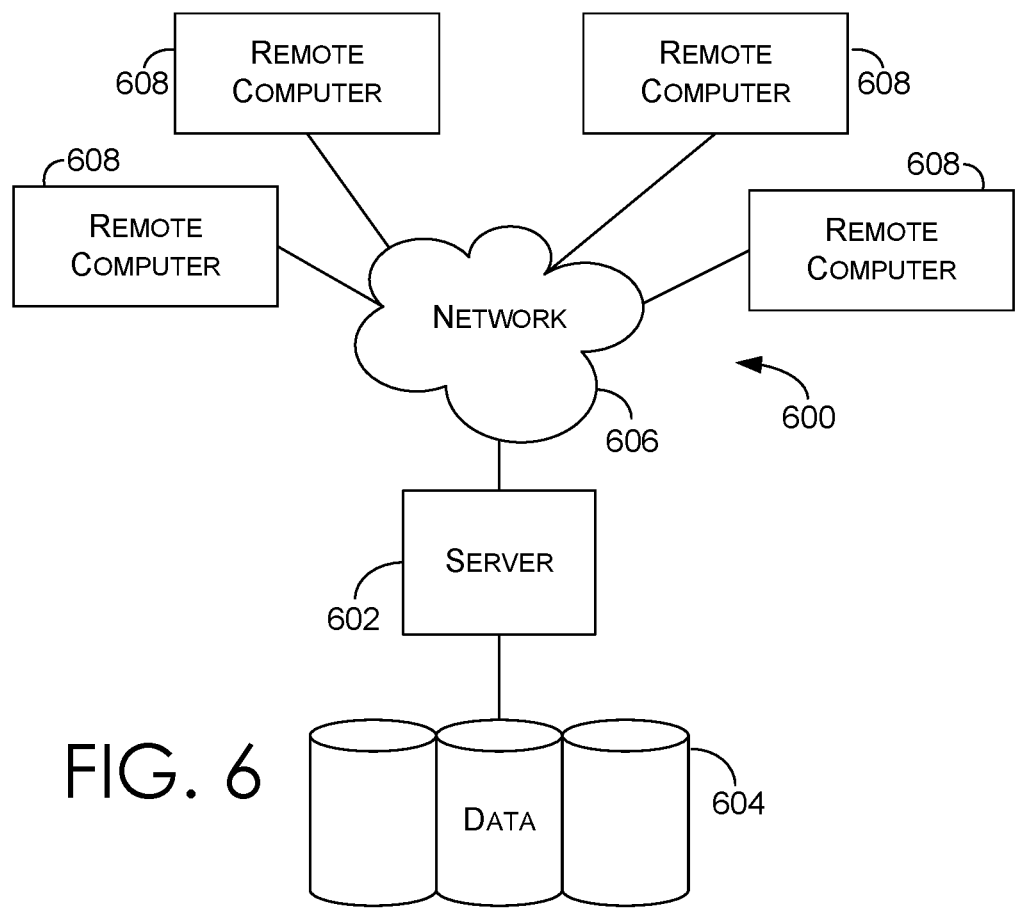
FIG. 6 depicts a block diagram of an exemplary computing environment suitable to implement embodiments of the present invention.

Hereinafter, an exemplary computing environment is described with regard to the systems, methods, and computer-media described hereinabove. Turning to FIG. 6, an exemplary computing environment is depicted, in accordance with an embodiment of the present invention. It will be understood by those of ordinary skill in the art that the exemplary computing environment 600 is just one example of a suitable computing environment and is not intended to limit the scope of use or functionality of the present invention. Similarly, the computing environment 600 should not be interpreted as imputing any dependency and/or any requirements with regard to each component and combination(s) of components illustrated in FIG. 6. It will be appreciated by those having ordinary skill in the art that the connections illustrated in FIG. 6 are also exemplary as other methods, hardware, software, and devices for establishing a communications link between the components, devices, systems, and entities, as shown in FIG. 6, may be utilized in implementation of the present invention. Although the connections are depicted using one or more solid lines, it will be understood by those having ordinary skill in the art that the exemplary connections of FIG. 6 may be hardwired or wireless, and may use intermediary components that have been omitted or not included in FIG. 6 for simplicity's sake. As such, the absence of components from FIG. 6 should be not be interpreted as limiting the present invention to exclude additional components and combination(s) of components. Moreover, though devices and components are represented in FIG. 6 as singular devices and components, it will be appreciated that some embodiments may include a plurality of the devices and components such that FIG. 6 should not be considered as limiting the number of a device or component.

Continuing, the computing environment 600 of FIG. 6 is illustrated as being a distributed environment where components and devices may be remote from one another and may perform separate tasks. The components and devices may communicate with one another and may be linked to each other using a network 606. The network 606 may include wireless and/or physical (e.g., hardwired) connections. Exemplary networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 606, generally, provides the components and devices access to the Internet and web-based applications.

The computing environment 600 comprises a computing device in the form of a server 604. Although illustrated as one component in FIG. 6, the present invention may utilize a plurality of local servers and/or remote servers in the computing environment 600. The server 602 may include components such as a processing unit, internal system memory, and a suitable system bus for coupling to various components, including a database or database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 602 may include or may have access to computer-readable media. Computer-readable media can be any available media that may be accessed by server 602, and includes volatile and nonvolatile media, as well as removable and non-removable media. By way of example, and not limitation, computer-readable media may include computer storage media and communication media. Computer storage media may include, without limitation, volatile and non-volatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 602. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In embodiments, the server 602 uses logical connections to communicate with one or more remote computers 608 within the computing environment 600. In embodiments where the network 606 includes a wireless network, the server 602 may employ a modem to establish communications with the Internet, the server 602 may connect to the Internet using Wi-Fi or wireless access points, or the server may use a wireless network adapter to access the Internet. The server 602 engages in two-way communication with any or all of the components and devices illustrated in FIG. 6, using the network 606. Accordingly, the server 602 may send data to and receive data from the remote computers 608 over the network 606.

Although illustrated as a single device, the remote computers 608 may include multiple computing devices. In an embodiment having a distributed network, the remote computers 608 may be located at one or more different geographic locations. In an embodiment where the remote computers 608 is a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some embodiments, the remote computers 608 is physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. In other embodiments, the remote computers 608 may be physically located in a non-medical setting, such as a packing and shipping facility or deployed within a fleet of delivery or courier vehicles.

Continuing, the computing environment 600 includes a data store 604. Although shown as a single component, the data store 604 may be implemented using multiple data stores that are communicatively coupled to one another, independent of the geographic or physical location of a memory device. Exemplary data stores may store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. Exemplary data stores may also store data in the form of electronic records, for example, electronic medical records of patients, transaction records, billing records, task and workflow records, chronological event records, and the like.

Generally, the data store 604 includes physical memory that is configured to store information encoded in data. For example, the data store 604 may provide storage for computer-readable instructions, computer-executable instructions, data structures, data arrays, computer programs, applications, and other data that supports the functions and action to be undertaken using the computing environment 600 and components shown in exemplary FIG. 6.

In a computing environment having distributed components that are communicatively coupled via the network 606, program modules may be located in local and/or remote computer storage media including, for example only, memory storage devices. Embodiments of the present invention may be described in the context of computer-executable instructions, such as program modules, being executed by a computing device. Program modules may include, but are not limited to, routines, programs, objects, components, and data structures that perform particular tasks or implement particular abstract data types. In embodiments, the server 602 may access, retrieve, communicate, receive, and update information stored in the data store 604, including program modules. Accordingly, the server 602 may execute, using a processor, computer instructions stored in the data store 604 in order to perform embodiments described herein.

Although internal components of the devices in FIG. 6, such as the server 602, are not illustrated, those of ordinary skill in the art will appreciate that internal components and their interconnection are present in the devices of FIG. 6. Accordingly, additional details concerning the internal construction device are not further disclosed herein.

Also, the present invention has been described in relation to particular embodiments, which are intended in all respects to be illustrative rather than restrictive. Thus the present invention is not limited to these embodiments, but variations and modifications may be made without departing from the scope of the present invention.

What is claimed is:

1. A computerized method comprising:
   receiving a plurality of records from one or more sources disparate from a first source;
   receiving at least one source record from the first source;
   calculating a probability of duplication for each of the plurality of records with respect to every other record of the plurality of records by utilizing one or more rules, wherein the one or more rules evaluate a variable of a field within the plurality of records to determine an outcome from a set of possible outcomes, wherein the set of possible outcomes comprises a match, a mismatch, and a determination that the variable is null, wherein the one or more rules assign a numerical value to the outcome for the probability of duplication;

classifying each of the plurality of records into a plurality of collections, wherein each of the plurality of collections includes one or more records having a probability of duplication of one another exceeding a predetermined threshold;

for each of the one or more records having the probability of duplication of one another that exceeds the predetermined threshold within each of the plurality of collections, weighting each record with a weight value;

identifying, from within each collection in the plurality of collections, a highest-weighted record having a highest numerical weight value within the collection;

generating a highest-weight collection that includes the highest-weighted record identified in each of the plurality of collections;

analyzing the highest-weight collection against the at least one source record from the first source; and based on analyzing the highest-weight collection, generating an updated set of records to write to the first source.

2. The method of claim 1, wherein each of the one or more sources is an electronic health record (EHR) system.

3. The method of claim 1, wherein the probability of duplication is a percentage value and the predetermined threshold is a configurable value.

4. The method of claim 1, wherein the one or more rules evaluate at least one variable of a field within a record.

5. The method of claim 4, wherein the one or more rules evaluating the at least one variable of the field within the record comprises associating each outcome of the at least one variable with a numeric value, wherein each outcome comprises a variable match, a variable mis-match, and a non-existent variable.

6. The method of claim 4, wherein the weight value is associated with at least one additional variable different from the at least one variable of the field within the record that is evaluated by the one or more rules.

7. The method of claim 4, wherein the weight value is associated with the at least one variable of the field within the record evaluated by the one or more rules.

8. The method of claim 1, wherein analyzing the highest-weight collection against the at least one source record of the first source comprises:

identifying whether the at least one source record of the first source is a duplicate of at least one other record in the highest-weight collection; and upon identifying that the at least one source record of the first source is a duplicate of the at least one other record, creating an updated record that includes content of the at least one source record and the at least one other record.

9. The method of claim 8, further comprising aggregating the updated record and any other records of the highest-weight collection into the updated set of records.

10. One or more non-transitory computer-readable media having executable instructions embodied thereon that, when executed by a processor of a computer device, perform a method, the method comprising:

receiving a plurality of records from one or more sources disparate from a first source;

receiving at least one source record from the first source;

calculating a probability of duplication for each of the plurality of records with respect to every other record of the plurality of records by utilizing one or more rules, wherein the one or more rules evaluate a variable of a field within the plurality of records to determine an outcome from a set of possible outcomes, wherein the set of possible outcomes comprises a match, a mismatch, and a determination that the variable is null, wherein the one or more rules assign a numerical value to the outcome and return a value for the probability of duplication;

classifying each of the plurality of records into a plurality of collections, wherein each of the plurality of collections includes one or more records having a probability of duplication of one another exceeding a predetermined threshold;

for each of the one or more records having the probability of duplication of one another that exceeds the predetermined threshold within each of the plurality of collections, weighting each record with a weight value;

identifying, from within each collection in the plurality of collections, a highest-weighted record having a highest numerical weight value within the collection;

generating a highest-weight collection that includes the highest-weighted record identified in each of the plurality of collections;

analyzing the highest-weight collection against the at least one source record from the first source; and based on analyzing the highest-weight collection, generating an updated set of records to write to the first source.

11. The media of claim 10, wherein each of the one or more sources is an electronic health record (EHR) system.

12. The media of claim 10, wherein the probability of duplication is a percentage value and the predetermined threshold is a configurable value.

13. The media of claim 10, wherein the one or more rules evaluate at least one variable of a field within a record.

14. The media of claim 13, wherein the one or more rules evaluating the at least one variable of the field within the record comprises associating each outcome of the at least one variable with a numeric value, wherein each outcome comprises a variable match, a variable mis-match, and a non-existent variable.

15. The media of claim 13, wherein the weight value is associated with at least one additional variable different from the at least one variable of the field within the record that is evaluated by the one or more rules.

16. The media of claim 13, wherein the weight value is associated with the at least one variable of the field within the record evaluated by the one or more rules.

17. The media of claim 10, wherein analyzing the highest-weight collection against the at least one source record of the first source comprises:

identifying whether the at least one source record of the first source is a duplicate of at least one other record in the highest-weight collection; and upon identifying that the at least one source record of the first source is a duplicate of the at least one other record, creating an updated record that includes content of the at least one source record and the at least one other record.

18. The media of claim 17, further comprising aggregating the updated record and any other records of the highest-weight collection into the updated set of records.

19. A system, the system comprising:
one or more processors configured to:
receive a plurality of records from one or more sources disparate from a first source;
receive at least one source record from the first source;

calculate a probability of duplication for each of the plurality of records with respect to every other record of the plurality of records by utilizing one or more rules, wherein the one or more rules evaluate a variable of a field within the plurality of records to determine an outcome from a set of possible outcomes, wherein the set of possible outcomes comprises a match, a mismatch, and a determination that the variable is null, wherein the one or more rules assign a numerical value to the outcome for the probability of duplication;

classifying each of the plurality of records into a plurality of collections, wherein each of the plurality of collections includes one or more records having a probability of duplication of one another exceeding a predetermined threshold;

for each of the one or more records having the probability of duplication of one another that exceeds the predetermined threshold within each of the plurality of collections, weight each record with a weight value;

identify, from within each collection in the plurality of collections, a highest-weighted record having a highest numerical weight value within the collection;

generate a highest-weight collection that includes the highest-weighted record identified in each of the plurality of collections;

analyze the highest-weight collection against the at least one source record from the first source; and based on the analysis of the highest-weight collection, generate an updated set of records to write to the first source.

20. The system of claim 19, wherein analyzing the highest-weight collection against the at least one source record of the first source comprises:

identifying whether the at least one source record of the first source is a duplicate of at least one other record in the highest-weight collection; and upon identifying that the at least one source record of the first source is a duplicate of the at least one other record, creating an updated record that includes content of the at least one source record and the at least one other record.

* * * * *